(12) United States Patent
Brandt et al.

(10) Patent No.: US 8,112,871 B2
(45) Date of Patent: Feb. 14, 2012

(54) METHOD FOR MANUFACTURING ELECTROSURGICAL SEAL PLATES

(75) Inventors: Kim V. Brandt, Laporte, CO (US); Allan G. Aquino, Longmont, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 128 days.

(21) Appl. No.: 12/568,282

(22) Filed: Sep. 28, 2009

(65) Prior Publication Data

US 2011/0073246 A1    Mar. 31, 2011

(51) Int. Cl.
*H01S 4/00* (2006.01)

(52) U.S. Cl. ............. 29/592.1; 29/825; 29/874; 29/876; 606/41; 606/45; 606/51; 606/52

(58) Field of Classification Search .................. 29/592.1, 29/825, 874, 876; 606/41, 45, 51, 52
See application file for complete search history.

(56) References Cited

U.S. PATENT DOCUMENTS

| | | | |
|---|---|---|---|
| 5,282,799 A | 2/1994 | Rydell | |
| 5,313,027 A | 5/1994 | Inoue et al. | |
| 5,512,721 A | 4/1996 | Young et al. | |
| 5,558,672 A | 9/1996 | Edwards et al. | |
| 5,562,720 A | 10/1996 | Stern et al. | |
| 5,569,241 A | 10/1996 | Edwards | |
| 5,792,137 A | 8/1998 | Carr et al. | |
| 5,810,764 A | 9/1998 | Eggers et al. | |
| 5,860,976 A | 1/1999 | Billings et al. | |
| 5,925,043 A | 7/1999 | Kumar et al. | |
| 6,106,542 A | 8/2000 | Toybin et al. | |
| 6,283,961 B1 | 9/2001 | Underwood et al. | |
| 6,508,815 B1 | 1/2003 | Strul et al. | |
| 6,558,385 B1 | 5/2003 | McClurken et al. | |
| 6,953,461 B2 | 10/2005 | McClurken et al. | |
| 6,958,070 B2 | 10/2005 | Witt et al. | |
| 7,179,255 B2 | 2/2007 | Lettice et al. | |
| 7,270,664 B2 * | 9/2007 | Johnson et al. | 606/51 |
| 7,276,068 B2 * | 10/2007 | Johnson et al. | 606/51 |
| 7,318,823 B2 | 1/2008 | Sharps et al. | |
| 7,931,649 B2 * | 4/2011 | Couture et al. | 606/51 |
| 2004/0030330 A1 | 2/2004 | Brassell et al. | |

(Continued)

FOREIGN PATENT DOCUMENTS

CA          2104423          2/1994

(Continued)

OTHER PUBLICATIONS

U.S. Appl. No. 12/336,970, filed Dec. 17, 2008.

(Continued)

*Primary Examiner* — Carl Arbes (57) ABSTRACT

A method of manufacture for an end effector assembly is provided. The method includes providing a pair of jaw members. A step of the method includes forming one or more seal plates positionable on one of the pair of jaw members. Etching a dam along a side of the one or more seal plates is a step of the method, wherein the etched dam inhibits the flow of a plastic on the one or more seal plate such that a height of the plastic with respect to the at least one seal plate during an overmolding process may be controlled. The method includes positioning the one or more seal plates on the one of the pair of jaw members; and overmolding the seal plate to one or more of the pair of jaw members.

15 Claims, 9 Drawing Sheets

U.S. PATENT DOCUMENTS

| | | | |
|---|---|---|---|
| 2004/0148035 A1 | 7/2004 | Barrett et al. |
| 2005/0033278 A1 | 2/2005 | McClurken et al. |
| 2006/0116675 A1 | 6/2006 | McClurken et al. |
| 2006/0283093 A1 | 12/2006 | Petrovic et al. |
| 2007/0016182 A1 | 1/2007 | Lipson et al. |
| 2007/0260235 A1 | 11/2007 | Podhajsky |
| 2009/0012520 A1 | 1/2009 | Hixson et al. |
| 2009/0082767 A1 | 3/2009 | Unger et al. |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 1159926 | 12/2001 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |

OTHER PUBLICATIONS

U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature, 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparabscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3. dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5.dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

METHOD FOR MANUFACTURING ELECTROSURGICAL SEAL PLATES

BACKGROUND

1. Technical Field

The present disclosure relates to a method and system for manufacturing electrosurgical seal plates and, more particularly, to a method and system that employs photolithographic processes and systems operatively associated therewith to manufacture seal plates.

2. Background of Related Art

Electrosurgical forceps, e.g., bipolar or monopolar forceps, are commonly known in the medical art. Typically, the electrosurgical forceps are configured to, amongst other things, grasp and subsequently seal tissue. With this purpose in mind, the electrosurgical forceps, typically, include a pair of movable jaw members each having a respective seal plate operatively disposed thereon.

Typically, the seal plates disposed on the jaw members are configured to transfer electrosurgical energy having one or more frequencies to tissue to electrosurgically treat the tissue (e.g., seal tissue) and, in conjunction with a cutting element (e.g., knife blade), subsequently sever the sealed tissue. In certain instances, the seal plates may be configured to maintain a certain gap distance between the seal plates when the jaw members are in a closed position and tissue is grasped therebetween. As can be appreciated by one skilled in the art, the seal plates may be configured to perform and/or provide additional functions not described herein.

To provide the seal plates with the capability to seal, subsequently sever, and/or maintain a desired gap distance, the seal plates frequently are designed to include one or more features operatively disposed thereon or formed therewith. For example, in the instance where the seal plates are configured to subsequently sever tissue, one or both of the seal plates may include a knife slot configured to receive a knife blade. In the instance where the seal plates are configured to maintain a desired gap distance, one or both of the seal plates may include one or more stop members. In either instance, forming the seal plates during the manufacture process requires extremely high precession, which may lead to high tolerance stack-ups (e.g., knife blade to knife slot width ratios). Additionally, conventional means for positioning a stop member on a seal plate include bonding the stop member to a seal surface of the seal plate. In this instance, however, the bond and/or stop member that secures the stop member to the seal surface of the seal plate is susceptible to shear stresses associated with opening and closing the jaw members of an end effector assembly.

Conventional manufacture processes for seal plates may include stamping, punching, blanking, embossing, bending, flanging, coining, etc. In some instances, however, these manufacturing process may not be suitable for unique and/or complex jaw member and/or seal plate geometries, such as, for example, when one or both of the seal plates requires a knife slot or stop member formed thereon. Additionally, manufacture of the seal plates via the aforementioned process, in certain instances, may not be cost effective.

SUMMARY

The present disclosure provides a method of manufacture for an end effector assembly configured for use with an electrosurgical instrument configured for performing an electrosurgical procedure. The method includes providing a pair of jaw members. A step of the method includes forming one or more seal plates positionable on one of the pair of jaw members. Etching a dam along a side of the one or more seal plates is a step of the method, wherein the etched dam inhibits the flow of a plastic on the one or more seal plate such that a height of the plastic with respect to the at least one seal plate during an overmolding process may be controlled. The method includes positioning the one or more seal plates on the one of the pair of jaw members; and overmolding the seal plate to one or more of the pair of jaw members.

The present disclosure provides a method of manufacture for an end effector assembly configured for use with an electrosurgical instrument configured for performing an electrosurgical procedure. The method includes providing a pair of jaw members. A step of the method includes forming one or more seal plates positionable on one or more of a pair of jaw members associated with the end effector assembly. Etching a dam along a side of the one or more seal plates is a step of the method, wherein the etched dam inhibits the flow of a plastic on the one or more seal plates such that a height of the plastic with respect to the one or more seal plates during an overmolding process may be controlled. Etching a targeted retention feature along the side of the one or more seal plates is another step of the method. Etching one or more pockets on a seal surface of the one or more seal plates is yet another step of the method. The method includes depositing an adhesive into the one or more pockets on the one or more seal plates. A step of the method includes transferring a spacer from a location remote from the one or more pockets on the one or more seal plates to the one or more pockets on the at least one seal plate. Curing the adhesive and positioning the one or more seal plates on one of the pair of jaw members are steps of the method. Overmolding the seal plate to jaw member is still another step of the method.

The present disclosure also provides a system for the manufacture of an end effector assembly configured for use with an electrosurgical instrument configured for performing an electrosurgical procedure. The system includes a photolithography module configured to etch one or more pockets on a seal surface of the seal plate. The system includes a vacuum module configured to raise, transfer and lower a spacer from a location remote from the one or more pockets on the seal plate to the one or more pockets on the seal plate. The system includes an adhesive dispensing module configured to dispense an adhesive into the one or more pockets on the seal plate and allowing the adhesive to cure. The system may include an optical module configured to monitor a volume of adhesive dispensed within the one or more pockets and monitor placement of the spacer within the one or more pockets.

In an embodiment, the adhesive dispensing module includes a module to heat cure the adhesive after the spacer has been positioned within the at least one pocket.

In an embodiment, a retention feature is etched on the at least one seal plate and is configured to secure the at least one seal plate to at least one of a pair of jaw members of the end effector assembly.

In an embodiment, a knife slot is etched on the at least one seal plate and is configured to receive a knife blade of the electrosurgical instrument.

In an embodiment, one or both of the seal plate includes two or more materials laminated together, wherein the two or more materials is electrically conductive. In one particular embodiment, the two or more materials is selected from the group consisting of stainless steel, copper and ceramic. The copper may include etched heat sinks formed at predetermined locations on the at least one seal plate.

In an embodiment, the one or more seal plate includes a polyimide flex circuit, wherein the polyimide flex circuit is configured to provide electrical communication between the at least one seal plate and a source of electrosurgical energy. In one particular embodiment, the polyimide flex circuit includes a dialectic material having one or more etched through holes configured to create an electrical interconnection between the at least seal plate and the source of electrosurgical energy.

In an embodiment, one or both of the seal plates includes a textured surface, logo, and/or ruler etched thereon.

BRIEF DESCRIPTION OF THE DRAWINGS

Various embodiments of the present disclosure are described hereinbelow with references to the drawings, wherein.

DETAILED DESCRIPTION

Embodiments of the presently disclosed method and system are described in detail with reference to the drawing figures wherein like reference numerals identify similar or identical elements. As used herein, the term "distal" refers to that portion which is further from the user while the term "proximal" refers to that portion which is closer to the user.

The method and system of the present disclosure implements photolithographic processes in combination with etching processes to create specific, unique, complex geometries and/or features for seal plates used in the design of electrosurgical instruments, such as, for example, bipolar and monopolar electrosurgical devices. For example, possible features may include knife blade slots, recessed features, fine delicate features, and half etched features; all of which to be discussed in greater detail below. In addition to creating the aforementioned features, the precision of etching allows for greatly reduced tolerance stack-ups which could reduce issues with, for example, knife blade to knife slot ratios. Moreover, because the seal plates of the present disclosure are formed via suitable photolithographic and etching processes, the seal plates may be processed in lead frames that may be used in automated processes, which reduces costs associated with the aforementioned conventional manufacturing processes (e.g., stamping). Further, etch recipes associated with a given etch process, allow a user to enter practical data relating to the seal plate that may facilitate forming the seal plate during the etch process. For example, etch recipes associated with a given etch process may be tuned to have both vertical and non-vertical profiles, such as, when forming a knife slot on the seal plate.

Figure 1:
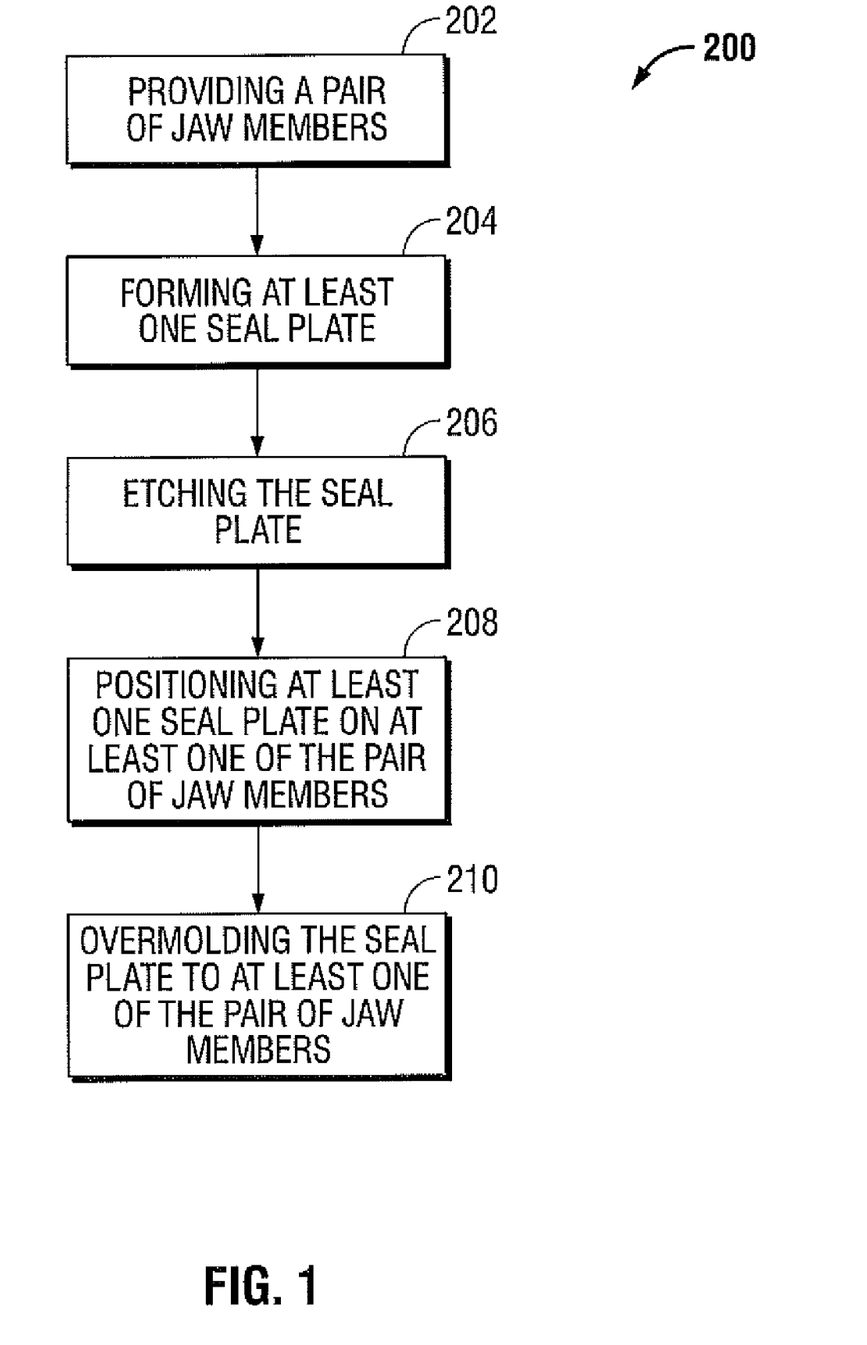
FIG. 1 is a flowchart illustrating steps for manufacturing a seal plate in accordance with an embodiment of the present disclosure.

With reference to FIG. 1, a flowchart illustrating a method of manufacture for an end effector assembly that includes a pair of jaw members each including a seal plate disposed thereon and configured for use with an electrosurgical instrument, e.g., electrosurgical forceps, in accordance with an embodiment of the present disclosure is shown designated 200.

An initial step of the method 200 includes providing a pair of jaw members (step 202) associated with an end effector adapted to connect to an electrosurgical forceps, such as, for example, a bipolar forceps. The jaw members may be formed by any suitable means, e.g., molding, casting, stamping, etc.

So as not to obscure the following disclosure with redundant information, manufacture of the seal plate is described herein as a single seal plate formed from a single sheet of material. Those skilled in the art will appreciate that a plurality of seal plates may be manufactured from a single sheet of material.

Figure 2:
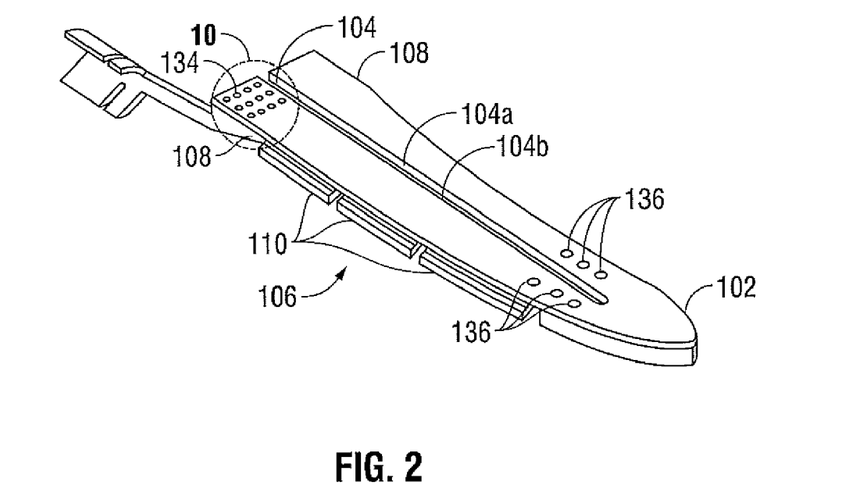
FIG. 2 is a side, perspective view of a seal plate according to an embodiment of the present disclosure and formed via the method of FIG. 1.
Figure 3A:
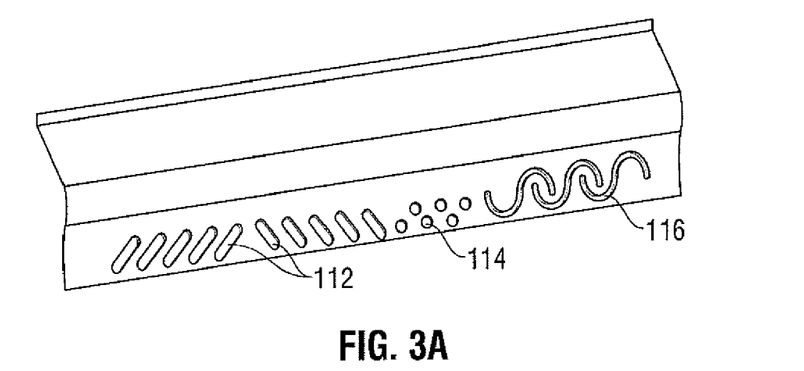
FIGS. 3A and 3B are perspective views of a seal plate according to an alternate embodiment of the present disclosure and formed via the method of FIG. 1.
Figure 3B:
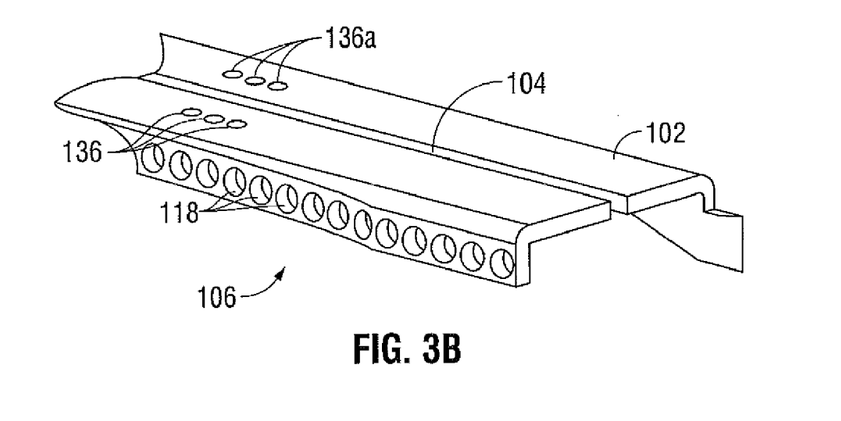

A step of method 200 includes forming a seal plate 102 (see step 204, in FIG. 1). Seal plate 102 may be formed from any suitable material, such as, for example, from a sheet of metal. A seal plate 102 formed according to method 200 is shown in FIG. 2. During formation of seal plate 102, seal plate 102 may be fully or partially etched (see step 206, in FIG. 1). For example, seal plate 102 may be etched to include one or more types of retention features 106. In the embodiment illustrated in FIG. 2, retention features 106 include a plurality etched flanges 110 that extend along one of a pair of sides 108 of the seal plate 102. In embodiments, retention features 106 may be partially etched in and/or fully etched through the seal plate 102. An example of partially etched retention features 106 is illustrated in FIG. 3A. More particularly, the partially etched retention features may be partially etched slots 112, partially etched cavities 114, and/or partially etched curved channels 116. An example of fully etched retention features 106 is illustrated in FIG. 3B. More particularly, the fully etched retention features 106 may be fully etched apertures 118. In either of the embodiments illustrated in FIGS. 2-3B, retention features 106 may be configured to securely retain the seal plate 102 to a respective jaw member of an end effector assembly associated with an electrosurgical forceps.

A step of method 200 includes positioning the seal plate 102 on a respective jaw member and subsequently overmolding the seal plate 102 to a respective jaw member (see steps 208 and 210 respectively in FIG. 1). In an embodiment, the photolithographic and etch processes in accordance with the method 200 of the present disclosure may be implemented to create partial etch dams along a side 108 of the seal plate 102.

Figure 4:
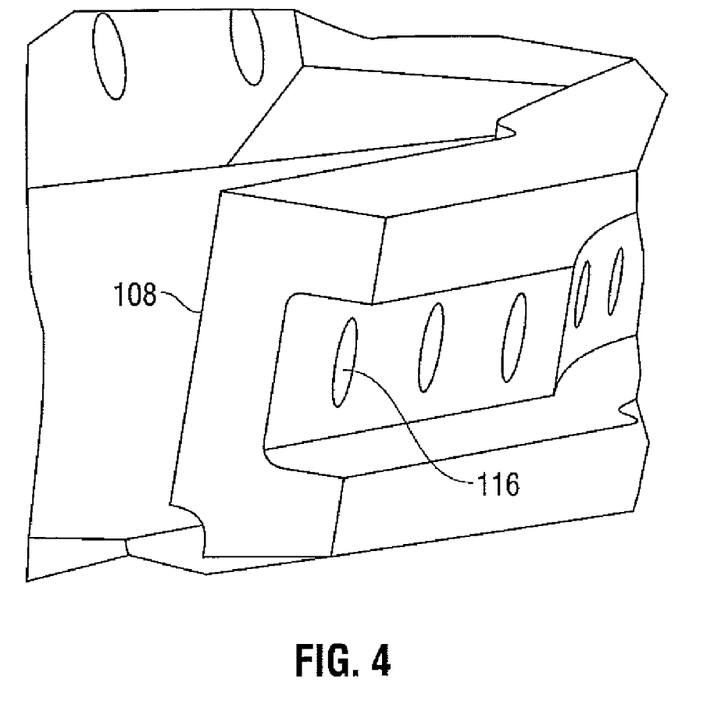
FIG. 4 is a perspective view of a seal plate according to an alternate embodiment of the present disclosure and formed via the method of FIG. 1.

More particularly, one or more partial etch dams 116 may be disposed and/or formed along one of the sides 108 of seal plate 102, see FIG. 4. Partial etch dam 116 is configured to control the height of an overmold during the overmolding process of the seal plate 102 to a respective jaw member of the end effector assembly. More particularly, the partial dam 116 is configured to inhibit the flow of a plastic during the overmolding process ensuring that the height of the plastic does not exceed a predetermined height on the seal plate 102 and/or the respective jaw member. Controlling and/or preventing the height of the plastic from exceeding a predetermined height on the seal plate 102 and/or a respective jaw member, e.g., jaw member 110 or 120, during the overmolding process, minimizes or "tightens" distribution of thermal spread during an electrosurgical procedure, e.g., electrosurgical sealing procedure. More particularly, the partial etch dam 116 creates a seal plate 102 having a consistent height across a length of the seal plate 102, which, in turn, provides a consistent seal across tissue and minimizes thermal spread to adjacent tissue. Experimentation on urethane coating processes confirms a relationship between seal plates having consistent (or inconsistent) seal plate heights and thermal spread. More particularly, thermal spread as a result of seal plates having consistent heights across a length of the seal plate was negligible when compared to seal plates having inconsistent heights across a length of the seal plate.

Figure 10:
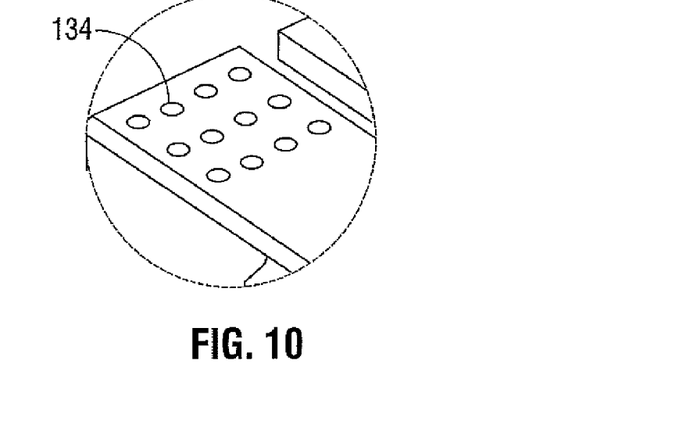
FIG. 10 is an area of detail of the seal plate illustrated in FIG. 1.

In an embodiment, the photolithographic and etching processes in accordance with the method 200 of the present disclosure may be employed to create one or more textured patterns on the seal plate 102. More particularly, one type of textured pattern may include, for example, a textured pattern 134 having a plurality of raised dots with varying dimensions etched on a portion of a seal surface 102a of the seal plate 102, see FIGS. 2 and 10.

Figure 5A:
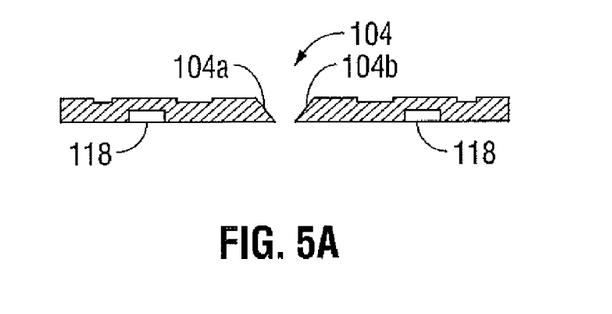
FIGS. 5A and 5B are respective cross-sectional views of a seal plate shown in a pre-formed and formed condition according to an alternate embodiment of the present disclosure and formed via the method of FIG. 1.
Figure 5B:
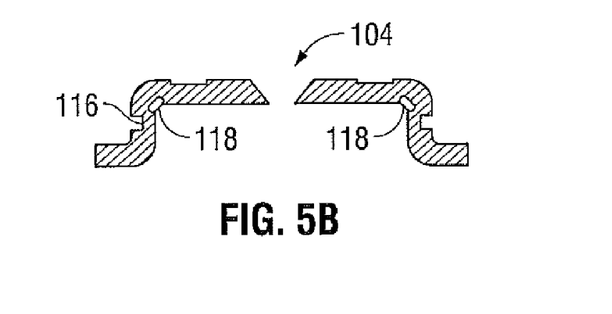
Figure 6:
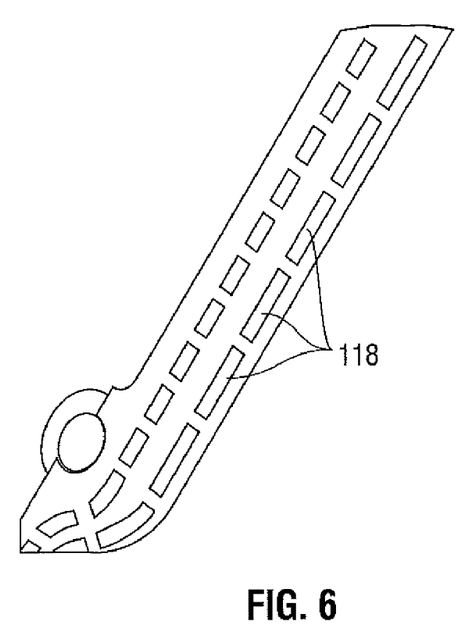
FIG. 6 is a perspective view of the seal plate of FIGS. 5A and 5B.
Figure 7:
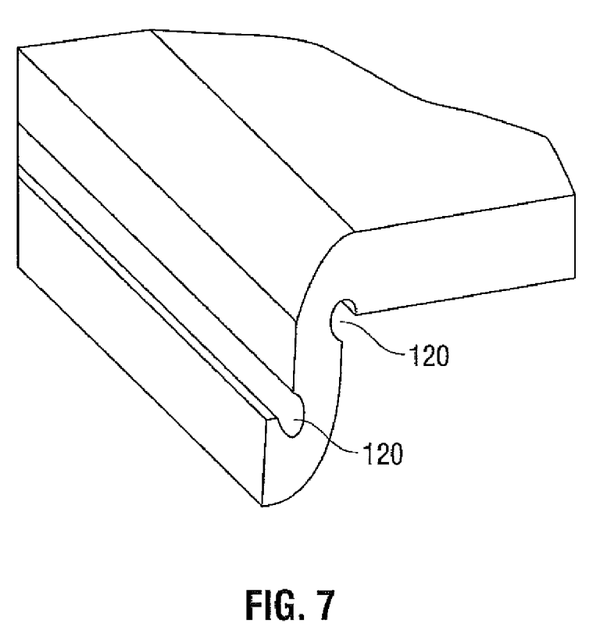
FIG. 7 is a perspective view of a seal plate according to an alternate embodiment of the present disclosure and formed via the method of FIG. 1.

With reference to FIGS. 5A and 5B, seal plate 102 is illustrated pre-formed and formed, respectively. In an embodiment, the photolithographic and etching processes in accordance with the method 200 of the present disclosure may be implemented to facilitate fanning of the seal plate 102. More particularly, selectively and/or partially etching the seal plate 102 lightens the overall structure of the seal plate 102, which, in turn, facilitates bending of the seal plate 102 during the forming process. To this end, one or more areas of the seal plate 102 may be selectively and/or partially etched. More particularly, selectively and/or partially etched areas 118 of the seal plate 102 may be located at predetermined locations on the seal plate 102, see FIGS. 5A and 6. Additionally, partial etching may be implemented to create curves 120 with small, tight radii, see FIGS. 5B and 7, which also makes forming seal plate 102 easier.

With reference again to FIG. 2, in an embodiment, the photolithographic and etching processes in accordance with the method 200 of the present disclosure may be implemented to create a knife slot 104 on the seal plate 102. More particularly, a knife slot 104 may be fully etched through the seal plate 102. The high precision that is associated with known photolithographic and etching processes, allows a manufacturer to form a fully etched knife slot 104 with various geometries. More particularly, in embodiments, the fully etched knife slot 104 may be defined by a pair of inner facing walls 104a and 104b. Inner facing walls 104a and 104b may be etched to have any suitable configuration. The precise configuration of the inner facing walls 104a and 104b may be determined by a manufacturer and subsequently entered into an etch recipe for a given etch process. In the embodiment illustrated in FIG. 2, inner facing walls 104a and 104b are illustrated perpendicular with respect to the seal surface 102b of the seal plate 102. In the embodiment illustrated in FIGS. 5A and 5B, inner facing walls 104a and 104b are illustrated slanted or angled with respect to the seal surface 102b of the seal plate 102.

Figure 8:
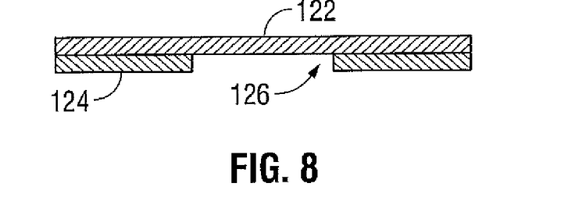
FIG. 8 is a cross-sectional view of a laminated seal plate according to an alternate embodiment of the present disclosure and formed via the method of FIG. 1.
Figure 9A:
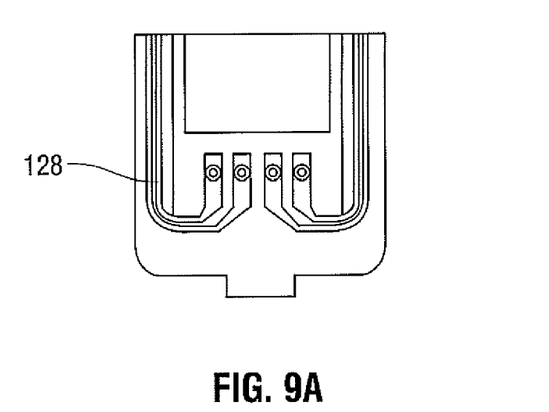
FIGS. 9A-9C is a seal plate including one or more points of electrical contact according to an alternate embodiment of the present disclosure and formed via the method of FIG. 1.
Figure 9B:
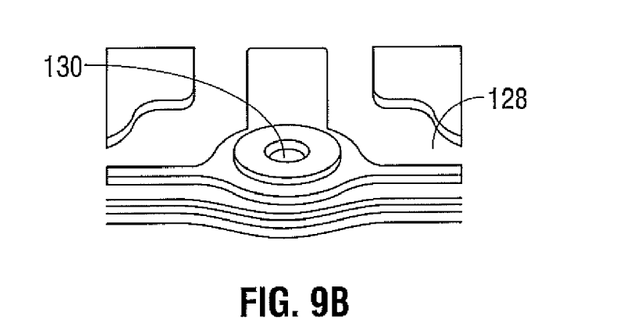
Figure 9C:
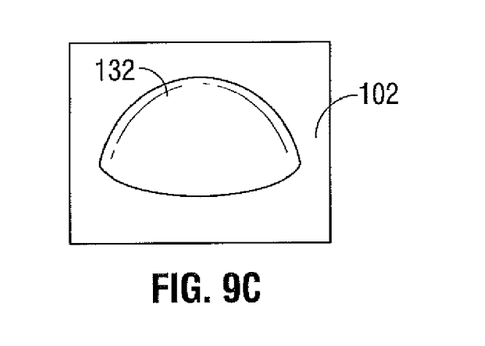

With reference to FIGS. 8-9B, in an embodiment, the photolithographic and etching processes in accordance with the method 200 of the present disclosure may be implemented to create selectively and/or partially etched areas on the seal plate 102 that are configured to provide one or more electrical points of contact on the seal plate 102 such that electrosurgical energy may be provided to the seal plate 102 and/or other electrical components associated therewith. More particularly, one or more materials may be laminated together and, subsequently, selectively and/or partially etched. The materials laminated together may be conductive, partially-conductive, or non-conductive. Suitable materials may include but are not limited to stainless steel, copper, silver, and the like.

In the embodiment illustrated in FIG. 8, a portion of the seal plate 102 includes layers of stainless steel 122 and copper 124 laminated together. In this embodiment, the layer of copper 124 is selectively etched. Etching the copper 124 in this manner may be used to create one or more etched areas 126 configured to receive one or more types of electrical interfaces. More particularly, an etched area 126 may be configured to receive integrated flex, e.g., a polyimide flex circuit 128 that is configured to provide electrosurgical energy to the seal plate 102, see FIG. 9A. In this instance, one or more through holes 130 may be fully etched to create electrical interconnections through dialectic material located on the polyimide flex (FIG. 9B). Additionally, seal plate 102 may include one or more partially or fully etched areas configured to receive a bead of solder 132 to create one or more electrical interconnections on the seal plate 102 which may result in electrical wiring being an integral component of the seal plate 102. In addition to the foregoing, laminating layers of material together and, subsequently, etching (e.g., partially or fully) one of the layers of material may be used to create heat sinks (not explicitly shown) at specific locations on the seal plate 102.

Figure 11A:
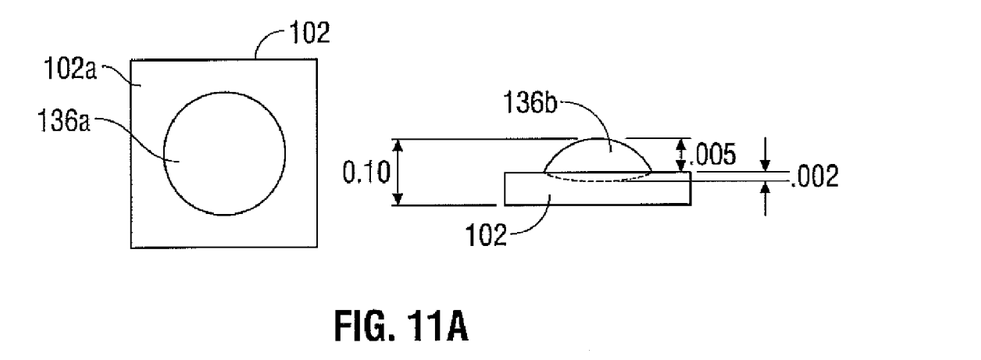
FIGS. 11A-11F are various configurations of spacers adapted for use with a seal plate formed via the method of FIG. 1.

As noted above, in certain instances the seal plates are configured to maintain a desired gap distance. With reference to FIGS. 11A-11F, in an embodiment, the photolithographic and etching processes in accordance with the method 200 of the present disclosure may be implemented to create one or more different types of insulation barriers, e.g., stop members, between seal plates associated with an end effector assembly More particularly, photolithographic and etching processes of the present disclosure may be implemented to create one or more partially or fully etched recesses or pockets 136a on seal surface 102a of the seal plate 102 (see FIG. 11A, for example), wherein the pockets 136a is configured to receive one or more types of corresponding spacers 136b (FIG. 11A). An etched recess 136a may include an etch depth of 0.002 inches. Spacer 136b may be any suitable type of spacer known in the art. Spacer 136 may extend from seal surface 102a a distance that ranges from about 0.005 inches to about 0.01 inches. In an embodiment, spacer 136b may be a ceramic spacer made from aluminum titanium carbide, commonly referred to in the art and hereinafter referred to as AlTiC).

Figure 11B:
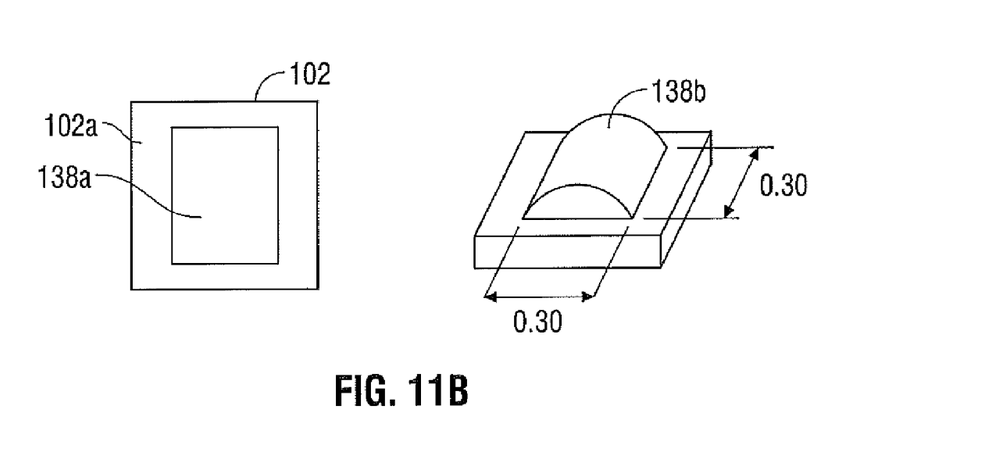
Figure 11C:
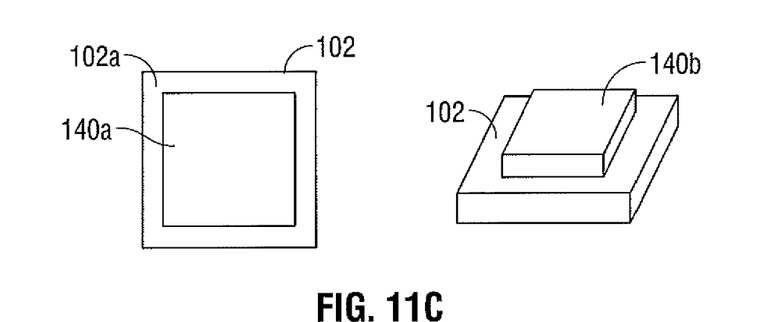
Figure 11D:
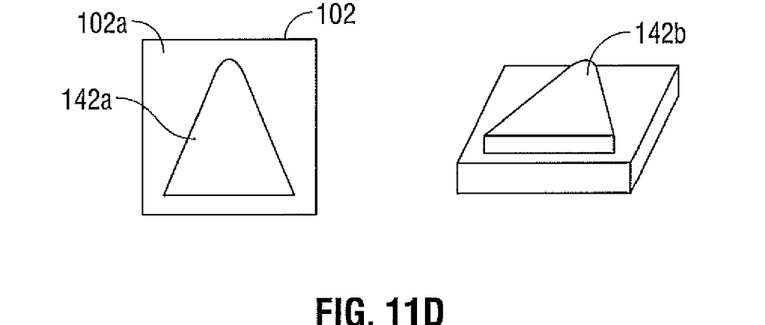
Figure 11E:
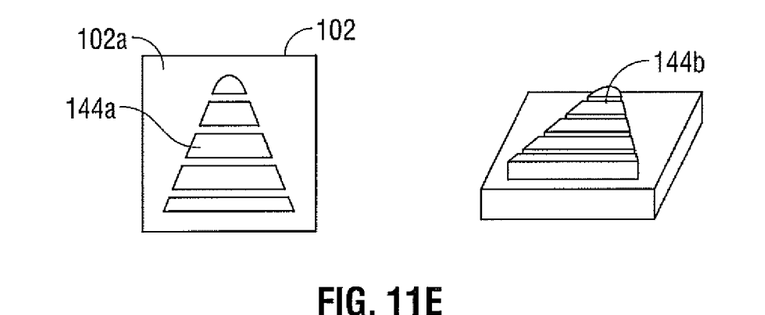
Figure 11F:
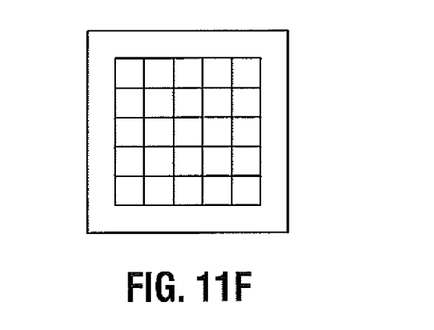

Etched recesses 136a and corresponding spacers 136b may have any suitable geometric configuration and may be dimension to fit within a 0.030×0.030 inch area (FIG. 11B). For example, FIG. 11A illustrates an etched recess 136a and corresponding spacer 136b each including a hemispherical configuration. FIG. 11B illustrates an etched recess 138a and corresponding spacer 138b each including a cylindrical configuration. FIG. 11C illustrates an etched recess 140a and corresponding spacer 140b each including a square configuration. FIG. 11D illustrates an etched recess 142a and corresponding spacer 142b each including a triangular configuration. FIG. 11E illustrates a plurality of etched recesses 144a and corresponding spacers 144b in an intermittent or staggered configuration. In embodiments, any of the aforementioned etched recesses and corresponding spacers may be arranged in a grid like configuration, see FIG. 11F for example. The combination of any of the aforementioned etched recesses, e.g., recess 138a and spacers, e.g., spacer 138b provides a user with the ability to manipulate how the jaw members 110 and 120 come together. For example, cylindrical shaped recess 138a and corresponding spacer 138b may be configured to force one of the jaw members, e.g., a upper jaw member 110 to roll along an axis of the spacer 138b when the upper jaw member 110 and a bottom jaw member 120 of an end effector assembly are moved toward each other, which, in turn, results in a more precise alignment of the upper and lower jaw members 110 and 120, respectively.

Moreover, the combination of any of the aforementioned etched recesses, e.g., recess 136a and spacers, e.g., spacer 136b increases the integrity of a bond between the seal surface 102a and spacer 136b in that the spacer 136b is encased within a recess 136b, as opposed to only being bonded to the seal surface 102a of the seal plate 102. The photolithographic and etching processes in accordance with the method 200 of the present disclosure allows a manufacturer to position any of the aforementioned spacers, e.g., spacer 136b within a corresponding pocket 136a to within a 0.0005 inch tolerance.

Figure 12:
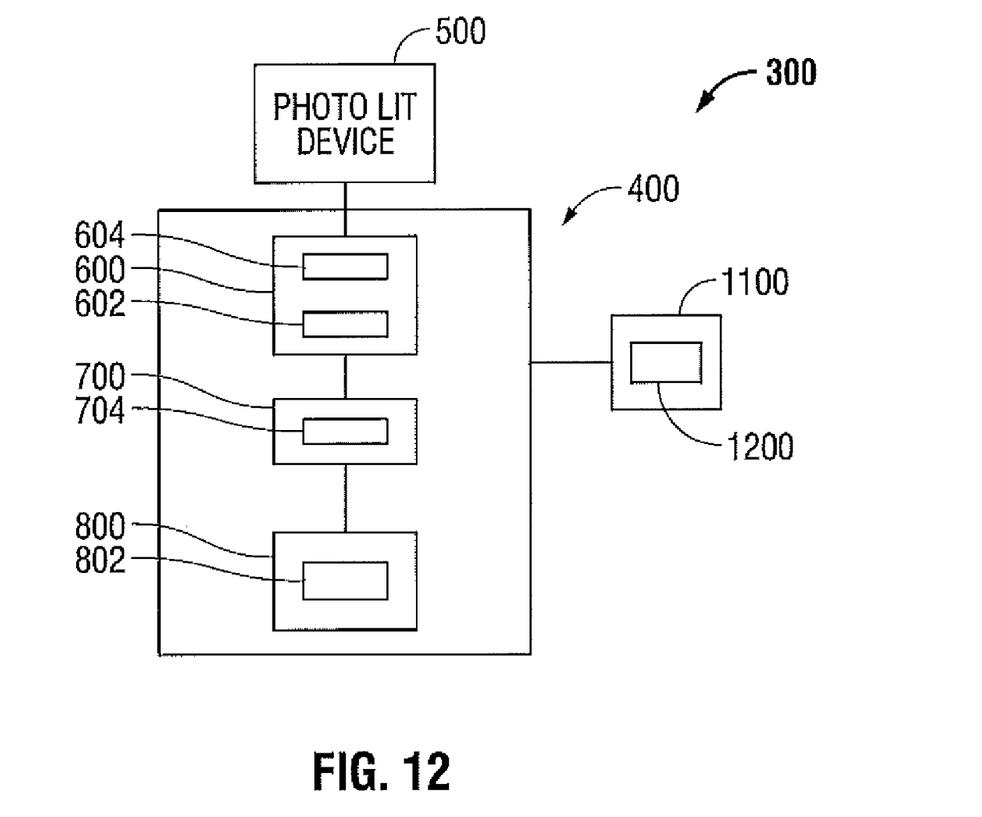
FIG. 12 illustrates a block diagram of a system adapted far use with the method of FIG. 1 and configured to position one of the various spacers depicted in FIGS. 11A-11F within a seal plate formed via the method of FIG. 1.
Figure 13A:
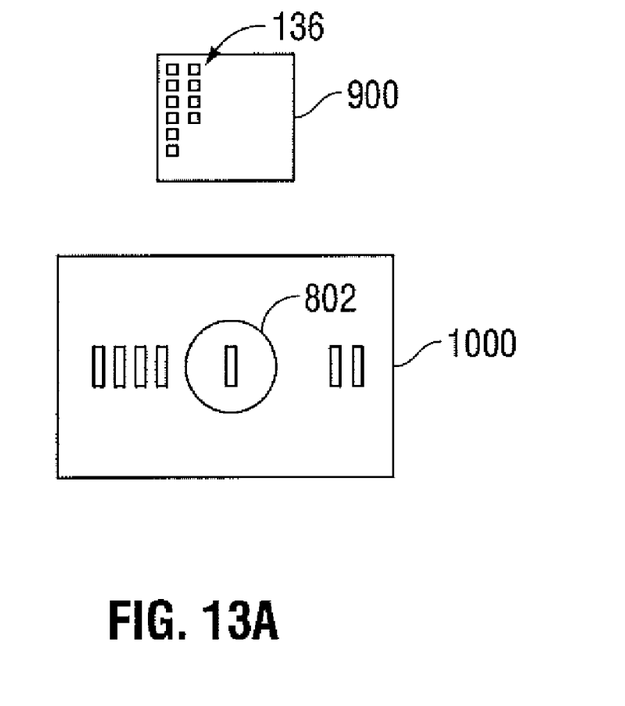
FIGS. 13A and 13B are functional block diagrams of a method of use of the system of FIG. 12.
Figure 13B:
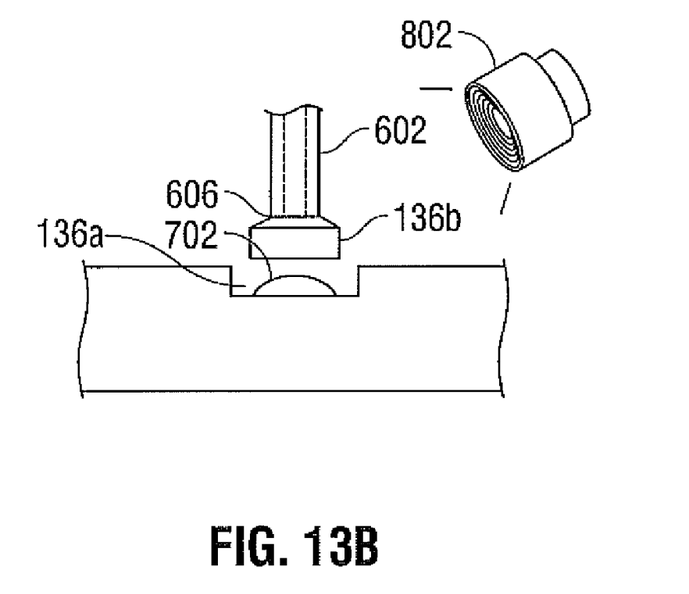

With reference now to FIGS. 12-13B, in an embodiment, a step of the method 200 may include etching one or more recesses, e.g., 136a on the seal surface 102a of the seal plate 102 and positioning a spacer, e.g., spacer 136b in the recess 136a. In this instance, an automated system 300 is provided and includes a plurality of modules 400 that includes a vacuum module 600, an adhesive dispensing module 700, and an optional optical module 800. Each of the foregoing modules is fully automated and in operative communication with a photolithography module 500 (configured to provide functions previously described herein) that is also fully automated.

Photolithography module 500 is configured to fully, partially, and/or selectively etch one or more pockets 136b on the seal surface 102a of the seal plate 102. After the pockets 136b have been etched into the seal surface 102a of the seal plate 102, the seal plate 102 is transferred to adhesive dispensing module 700 where a bead of adhesive 702 will be dispensed into the pocket 136b such that a spacer 136a may be positioned into the pocket 136b and bonded therein.

Vacuum module 600 is configured to raise and transfer a spacer, e.g., spacer 136b from a loading module 900 (a loading table 900, for example) to the one or more pockets 136a on the seal plate 102 and lower the spacer 136b within the pocket 136a on the seal plate 102. With this purpose mind, the vacuum module 600 includes one or more vacuum transfer devices 602 operatively connected to a vacuum source 604. Vacuum transfer device 602 may be any suitable device that is capable of raising, transferring and lowering a spacer 136b. For example, vacuum devices typically associated with the manufacture process of disk drives, auto slider bond, SMT automated assembly and PCB assembly may be utilized in combination with vacuum module 600. In an embodiment, the vacuum transfer device 602 (e.g., vacuum device typically utilized in the manufacture process PCB assembly) includes a distal end 606 configured to raise a spacer 136b (FIG. 13) from loading table 900, transfer the spacer 136b to the recess 136a, and, subsequently, lower the spacer 136b within the recess 136a.

Adhesive dispensing module 700 is configured to dispense a bead of suitable adhesive 702 into the one or more pockets 136a on the seal plate 102. In an embodiment, the adhesive dispensing module includes a device 704 configured to heat cure the adhesive 702 after the spacer 136b has been positioned within the pocket 136a.

In an embodiment, an optical module 800 is provided and is configured to monitor the volume of adhesive 702 dispensed within the pocket 136a, monitor alignment of the spacer 136b with respect to pocket 136a and/or monitor placement of the spacer 136b within the pocket 136a. To this end, optical module 800 may include one or more types of camera 802 located at or near the adhesive dispensing module 700.

System 300 includes one or more microprocessors 1100 including one or more algorithms 1200 configured to control and monitor each of the above-referenced modules during transferring and positioning of the spacers 136b within the pockets 136a. System 300 employs an x-y coordinate axis system to facilitate properly aligning a spacer 136b and pocket 136a (FIG. 13A).

In use, the vacuum transfer device 602 of vacuum module 600 is used to raise one of a plurality of spacers 136b from a loading table 900 to an adhesive station 1000 where the seal plate 102 is located. At a time prior to the spacer 136b arriving at the adhesive station 1000, adhesive dispensing module 700 dispenses a bead of adhesive 702 (FIG. 13B) within a pocket 136a. The time the bead of adhesive 702 is dispensed will depend on such parameters as type of adhesive, cure time of adhesive, volume of adhesive, etc. Camera 802 of optical module 800 may be employed to ensure that the spacer 136b and pocket 136a are properly aligned. Once it is determined that the spacer 136a and pocket 136b are properly aligned, the vacuum transfer device 602 may be employed to lower the spacer 136b into pocket 136a. Camera 802 of optical module 800 may again be employed to ensure that the spacer 136b seats at a proper height above pocket 136a (FIG. 13B). In accordance with the present disclosure spacer 136b seats at a height above the pocket 136a that ranges from about 0.001 inches to about 0.006 inches. Once it is determined that the spacer 136b seats at a proper height above pocket 136a, ultra violet heat may be applied to facilitate the curing process.

From the foregoing and with reference to the various figure drawings, those skilled in the art will appreciate that certain modifications can also be made to the present disclosure without departing from the scope of the same.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacture for an end effector assembly, the method including:
    forming at least one seal plate positionable on at least one of a pair of jaw members associated with the end effector assembly;
    etching a dam along a side of the at least one seal plate, wherein the etched dam inhibits the flow of a plastic on the at least one seal plate such that a height of the plastic with respect to the at least one seal plate during an overmolding process may be controlled;

etching a targeted retention feature along the side of the at least one seal plate;

etching at least one pocket on a seal surface of the at least one seal plate;

depositing an adhesive into the at least one pocket on the at least one seal plate;

transferring a spacer from a location remote from the at least one pocket on the at least one seal plate to the at least one pocket on the at least one seal plate;

curing the adhesive;

positioning the at least one seal plate on at least one of the pair of jaw members; and overmolding the seal plate to jaw member.

2. A method of manufacture for an end effector assembly according to claim 1, wherein the step of etching is performed via photolithographic process.

3. A method of manufacture for an end effector assembly according to claim 1, further including the step of etching a knife slot on the at least one seal plate.

4. A method of manufacture for an end effector assembly according to claim 1, wherein the step of forming at least one seal plate includes laminating at least two materials together, wherein at least one of the two materials is electrically conductive.

5. A method of manufacture for an end effector assembly according to claim 4, wherein the step of the at least two materials is selected from the group consisting of stainless steel, copper and ceramic.

6. A method of manufacture for an end effector assembly according to claim 1, wherein the step of etching includes selectively etching copper such that heat sinks are formed at predetermined locations on the at least one seal plate.

7. A method of manufacture for an end effector assembly according to claim 6, further including the step of securing a polyimide flex circuit to the at least one seal plate, wherein the polyimide flex circuit is configured to provide electrical communication between the at least one seal plate and a source of electrosurgical energy.

8. A method of manufacture for an end effector assembly according to claim 7, wherein the step of etching includes etching at least one through hole configured to create an electrical interconnection through a dialectic material on the polyimide flex circuit.

9. A method of manufacture for an end effector assembly according to claim 1, wherein the step of etching includes etching at least one of a textured surface, logo, and ruler on the at least one seal plate.

10. A method of manufacture for an end effector assembly according to claim 1, wherein the step of etching includes selectively etching at least a portion of the at least one seal plate to lighten the overall structure of the at least one seal plate, wherein selectively etching at least a portion of the at least one seal plate facilitates bending the at least one seal plate during the manufacture process of the at least one seal plate.

11. A method of manufacture for an end effector assembly according to claim 1, including the step of using a spacer that is formed from aluminum titanium carbide.

12. A method of manufacture for an end effector assembly according to claim 11, including the step of using a spacer that includes a configuration selected from the group consisting of hemispherical, cylindrical, square, and rectangular.

13. A method of manufacture for an end effector assembly according to claim 1, further including the step of positioning the spacer within the at least one pocket.

14. A method of manufacture for an end effector assembly according to claim 13, wherein the step of positioning the spacer within the at least one pocket includes using a vacuum source configured to transfer the spacer from the location remote the at least one pocket to the at least one pocket and deposit the spacer into the at least one pocket.

15. A method of manufacture for an end effector assembly according to claim 13, wherein the step of positioning the spacer within the at least one pocket includes using a camera to confirm a proper volume of adhesive has been deposited into the at least one pocket and the spacer is seated at a proper height within the at least one pocket.

\* \* \* \* \*